United States Patent [19]
Marshall et al.

[11] Patent Number: 4,769,482
[45] Date of Patent: Sep. 6, 1988

[54] CYANO AND THIOCYANO INTERMEDIATES

[75] Inventors: Winston S. Marshall, Bargersville, Ind.; John P. Verge, Henley-on-Thames, England

[73] Assignee: Eli Lilly and Company, Indianapolis, Ind.

[21] Appl. No.: 941,472

[22] Filed: Dec. 15, 1986

Related U.S. Application Data

[62] Division of Ser. No. 439,239, Nov. 3, 1982, Pat. No. 4,661,505.

[51] Int. Cl.$^4$ .................. C07C 161/02; C07C 121/76
[52] U.S. Cl. ..................................... 558/16; 558/404; 558/405

[58] Field of Search .......................... 558/404, 405, 16

[56] References Cited

U.S. PATENT DOCUMENTS 3,324,121  6/1967  Sprague ........................... 260/247.2

Primary Examiner—Glennon H. Hollrah
Assistant Examiner—D. B. Springer
Attorney, Agent, or Firm—Robert A. Conrad; Leroy Whitaker

[57] ABSTRACT

This invention provides novel alkane derivatives which are leukotriene antagonists, formulations of those derivatives, and a method of using those derivatives for the treatment of conditions characterized by an excessive release of leukotrienes.

5 Claims, No Drawings

CYANO AND THIOCYANO INTERMEDIATES

This application is a division of application Ser. No. 439,239, filed Nov. 3, 1982, U.S. Pat. No. 4,661,505.

BACKGROUND OF THE INVENTION

Research in the area of allergic reactions of the lung has provided evidence that arachidonic acid derivatives formed by the action of lipoxygenases are related to various disease states. Some of these arachidonic acid metabolites have been classified as members of a family of eicosatetraenoic acids termed leukotrienes. Three of these substances are currently thought to be major components of what has been previously called slow reacting substance of anaphylaxis (SRS-A).

It is the object of this invention to provide chemical agents which are selective leukotriene antagonists that can be used therapeutically in the treatment of allergic disorders such as asthma, where leukotrienes are thought to be causal mediators.

SUMMARY OF THE INVENTION

This invention provides for compounds of the Formula I

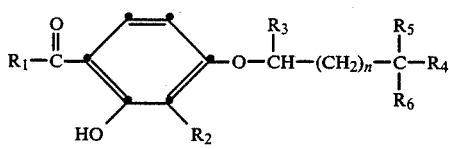

and pharmaceutically acceptable salts thereof, wherein:

$R_1$ is hydrogen, $C_1$–$C_6$ alkyl, $C_3$–$C_8$ cycloalkyl, or phenyl;

$R_2$ is hydrogen, $C_1$–$C_6$ alkyl, or $C_2$–$C_6$ alkenyl;

$R_3$ is hydrogen, $C_1$–$C_{10}$ alkyl, phenyl, $C_1$–$C_{10}$ alkyl-substituted phenyl, biphenyl, or benzylphenyl;

$R_4$ is —COOR$_7$, —CONR$_8$R$_9$, —CONHOH, hydroxy, —NR$_8$R$_9$, —SC(=NH)NH$_2$,

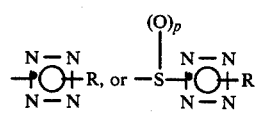

where $R_7$ is hydrogen or $C_1$–$C_4$ alkyl, $R_8$ and $R_9$ are each independently hydrogen, $C_1$–$C_3$ alkyl, or when taken together with the nitrogen atom form a morpholine or N-methyl piperazine ring, R is hydrogen, $C_1$–$C_4$ alkyl, or —CH$_2$COOR$_7$, and p is 0, 1, or 2;

$R_5$ and $R_6$ are each independently hydrogen or $C_1$–$C_3$ alkyl;

and n is 0–10.

Additionally provided by this invention are the compounds of formula I'

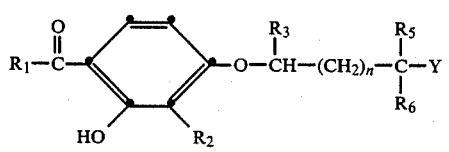

wherein Y is —CN or —SCN and $R_1$, $R_2$, $R_3$, $R_5$, $R_6$, and n are the same as previously defined. These compounds are useful as intermediates in the preparation of certain of the other compounds of this invention.

Further provided by this invention is a method for treating immediate hypersensitivity conditions such as asthma, using compounds of Formula I above and pharmaceutical formulations for these compounds.

DETAILED DESCRIPTION AND PREFERRED EMBODIMENT

The present invention relates to new organic compounds that are useful in the treatment of immediate hypersensitivity reactions. A preferred group of compounds are the compounds of Formula I wherein:

(a) $R_1$ is $C_1$–$C_6$ alkyl, especially methyl,
(b) $R_2$ is $C_1$–$C_6$ alkyl, especially propyl,
(c) $R_2$ is $C_3$–$C_6$ alkenyl, especially allyl,
(d) $R_3$ is hydrogen,
(e) $R_5$ is hydrogen,
(f) $R_6$ is hydrogen,
(g) $R_4$ is —COOH,
(h) $R_4$ is 5-tetrazolyl (R is hydrogen),
(i) $R_4$ is 5-thiotetrazolyl (R is hydrogen and p is 0), and
(j) n is 1–4, especially where n is 1 or 2.

Especially preferred compounds of Formula I are those wherein $R_1$ is methyl and $R_2$ is propyl. Also especially preferred are those compounds wherein $R_4$ is 5-tetrazolyl (R is hydrogen), 5-thiotetrazolyl (R is hydrogen and p is 0), or —COOH.

The following definitions refer to the various terms used throughout this disclosure.

The term "$C_1$–$C_{10}$ alkyl" refers to the straight and branched aliphatic radicals of 1 to 10 carbon atoms such as methyl, ethyl, propyl, isopropyl, butyl, isobutyl sec-butyl, tert-butyl, amyl, isoamyl, sec-amyl, sec-isoamyl (1,2-dimethylpropyl), tert-amyl (1,1-dimethylpropyl), hexyl, isohexyl (4-methylpentyl), sec-hexyl (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, ·1,2,2-trimethylpropyl, 1,1,2trimethylpropyl, heptyl, isoheptyl (5-methylhexyl), sec-heptyl (1-methylhexyl), 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, isooctyl (6-methylheptyl), sec-octyl (1-methylheptyl), tert-octyl (1,1,3,3-tetramethylbutyl), nonyl, 1-, 2-, 3-, 4-, 5-, 6-, or 7-methyloctyl, 1-, 2-, 3-, 4-, or 5-ethylheptyl, 1-, 2-, or 3-propylhexyl, decyl, 1-, 2-, 3-, 4-, 5-, 6-, 7-, or 8-methylnonyl, 1-, 2-, 3-, 4-, 5-, or 6-ethyloctyl, 1-, 2-, 3-, or 4-propylheptyl, and the like. The term "$C_1$–$C_{10}$ alkyl" includes within its definition the term "$C_1$–$C_3$ alkyl", "$C_1$–$C_4$ alkyl", and "$C_1$–$C_6$ alkyl".

The term "$C_3$–$C_8$ cycloalkyl" refers to the saturated alicyclic rings of three to eight carbon atoms such as cyclopropyl, methylcyclopropyl, cyclobutyl, cyclopentyl, cyclohexyl, cyclooctyl, and the like.

The term "$C_2$–$C_6$ alkenyl" refers to straight and branched radicals of two to six carbon atoms such as ethenyl, allyl, isopropenyl, butenyl, isobutenyl, 3-methyl-2-butenyl, n-hexenyl, and the like, and includes the term "$C_3$–$C_6$alkenyl".

The pharmaceutically acceptable base addition salts of this invention include salts derived from inorganic bases, such as ammonium and alkali and alkaline earth metal hydroxides, carbonates, bicarbonates, and the like, as well as salts derived from non-toxic basic organic amines, such as aliphatic and aromatic amines, aliphatic diamines, hydroxy alkylamines, and the like. Such bases useful in preparing the salts of this invention thus include ammonium hydroxide, potassium carbonate, sodium bicarbonate, calcium hydroxide, methyl amine, diethyl amine, ethylene diamine, cyclohexylamine, ethanolamine, and the like. The potassium and sodium salt forms are particularly preferred.

In addition, when the compounds of formula I are amine derivatives (e.g, $R_4$ is —$NR_8R_9$ or —$SC(=NH)NH_2$), the compounds may also exist as the corresponding acid addition salts. The pharmaceutically acceptable acid addition salts of this invention therefore also include salts derived from inorganic acids such as hydrochloric acid, nitric acid, phosphoric acid, sulfuric acid, hydrobromic acid, hydroiodic acid, phosphorous acid and the like, as well as salts derived from nontoxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4dioate, hexyne-1,6-dioate, benzoate, chlorobenzoate, methylbenzoate, dinitrobenzoate, hydroxybenzoate, methoxybenzoate, phthalate, terphthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate, and the like salts. Salts from inorganic acids are preferred, especially the hydrochloride or hydrobromide salts.

It is recognized that if $R_3$ is other than hydrogen and/or if $R_5$ is different from $R_6$, various stereoisomers will exist. This invention is not limited to any particular stereoisomer but includes all possible individual isomers and racemates of the compounds of Formula I.

The compounds of this invention may be prepared by the reaction of a phenol of the formula

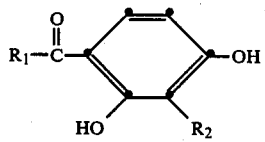

wherein $R_1$ and $R_2$ are described hereinabove, with a compound of the formula

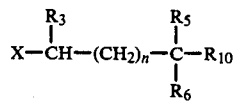

wherein $R_3$, $R_5$, $R_6$, and n are as described hereinabove, X is a suitable leaving group, such as halo, and $R_{10}$ is hydroxy, a protected acid ester, such as —$COO(C_1-C_4$ alkyl) or a benzhydryl ester, or is cyano or thiocyano. The reaction between compounds II and III is usually performed in equimolar amounts although ratios other than equimolar amounts are completely operative. The reaction is best carried out in a nonreactive solvent such as ketones, especially acetone or methyl ethyl ketone, and in the presence of a base, preferably an alkali metal hydroxide or carbonate, preferably potassium carbonate. Especially when X is chloro, a catalyst such as potassium or sodium iodide may be added to increase the reaction rate. The reaction may be carried out at temperatures of about ambient temperature up to the boiling point of the reaction mixture, the latter being preferred.

In the case where $R_{10}$ is cyano, the resulting derivative of Formula I' may be converted to the compounds of this invention by the following methods. Compounds of Formula I wherein $R_4$ is —COOH may be obtained by hydrolysis of the intermediate cyano derivative. This is generally accomplished by heating the cyano derivative in aqueous alcohols in the presence of a base such as sodium hydroxide. Alternatively, the carboxylic acid derivatives (I, $R_4$ is —COOH) may be prepared by the hydrolysis of the corresponding ester derivatives. This may be accomplished by an aqueous hydrolysis as described above or, especially in the case of a diphenylmethyl (benzhydryl) ester, using such methods known in the art such as treating with formic acid and triethylsilane followed by an aqueous workup, acidic hydrolysis, treatent with trifluoroacetic acid in anisole, or catalytic hydrogenation. The required benzhydryl ester starting materials (III, $R_{10}$ is a benzhydryl ester) may be prepared from the corresponding carboxylic acids (III, $R_{10}$ is —COOH) in the usual ways, such as treatment with diphenyldiazomethane in methylene chloride or heating with benzhydrol and a mineral acid in a solvent such as toluene with the azeotropic removal of water. The compounds of Formula I wherein $R_4$ is —$COOR_7$ and $R_7$ is $C_1-C_4$ alkyl may be prepared by conventional methods of esterification from the respective acid derivatives or are prepared directly by the methods described below. Salts may be prepared by treating the corresponding acids ($R_4$ is —COOH) with an appropriate base in the normal manner. Amide derivatives ($R_4$ is —$CONR_8R_9$ or —CONHOH) may be prepared by direct aminolysis of the corresponding ester, or from the corresponding carboxylic acid using conventional means such as conversion to the acid chloride followed by reaction of the acid chloride with an appropriate amine or treatment with an agent such as 1,1'-carbonyldiimidazole in the presence of an appropriate amine. In either case, the ester or acid is reacted with the appropriate amine VI $$HNR_8R_9 \qquad VI$$

wherein $R_8$ and $R_9$ are as described hereinabove, or hydroxylamine, the latter giving the hydroxamic acid derivative.

The compounds of Formula I wherein $R_4$ is 5-tetrazolyl (R is hydrogen) are prepared by treating the cyano intermediate with an alkali metal azide such as sodium azide, ammonium chloride, and (optionally) lithium chloride in a non-reactive high-boiling solvent such as N,N-dimethylformamide, preferably at temperatures from 60° C. to the reflux teperature of the reaction mixture. The thiotetrazole compounds of Formula I are prepared from the thiocyano intermediates in a similar manner.

Alternatively the compounds of Formula I may be prepared by the reaction of the phenol of Formula II with a compound of the Formula IV

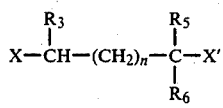

wherein $R_3$, $R_5$, $R_6$, and n are the same as described hereinabove and X and X' are the same or different leaving groups, such as halo. The resulting products are those having the formula

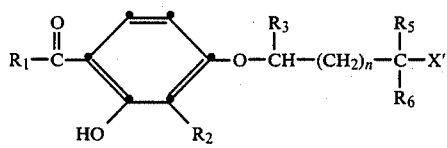

wherein $R_1$, $R_2$, $R_3$, $R_5$, $R_6$, n, and X' are the same as described hereinabove. As those skilled in the art will recognize, when the substituents $R_3$, $R_5$, and $R_6$ afford a symmetrically-substituted dihaloalkane IV, X and X' may be the same or different leaving groups since the reaction with phenol II will give the same product V regardless which "end" of the molecule reacts. However, when alkane IV is non-symmetrically substituted, those skilled in the art will recognize that X should be a better leaving group than X' in order for the desired product V to be formed. If X' is the better leaving group in compound IV, IV can first be converted to a compound such as III (e.g., reaction of IV with an alkali metal cyanide to give III where $R_{10}$ is —CN) which can then be reacted with phenol II as previously described.

The compounds of Formula V may be transformed into the compounds of this invention in the following manner. When compounds of Formula V are heated with an alkali metal cyanide, such as sodium cyanide, in the presence of a high boiling, nonreactive solvent, such as N,N-dimethylformamide, at elevated temperatures (50° C. to the reflux temperature of the solvent), the intermediate cyano compound of Formula I' is produced which may then be transformed into the acid, ester, or tetrazole derivatives as described previously. Similarly, the thiotetrazole compounds of this invention can be prepared by reacting a compound of Formula V with an alkali metal thiocyanate in a similar manner to give the intermediate thiocyano compound of Formula I', followed by transformation to the thiotetrazole in the usual manner.

The compounds of Formula I wherein $R_4$ is —OH may be prepared directly from the reaction of phenol II and a haloalkanol (III, X is halo, $R_{10}$ is —OH) or may be prepared from the intermediate V by aqueous hydrolysis.

The compounds of Formula I wherein $R_4$ is $-NR_8R_9$ may be prepared by the reaction of the compounds of Formula V with compounds of the formula VI. The reaction of compounds V and VI is generally carried out in the presence of a nonreactive, high-boiling solvent such as N,N-dimethylformamide, usually in the presence of a base, preferably an alkali metal carbonate or hydroxide, generally at elevated temperatures up to the boiling point of the solvent.

The isothiourea and thiotetrazole compounds may be prepared from intermediate V by reacting with thiourea and 5-mercaptotetrazole, respectively. In either case, the reaction is performed by stirring the two reactants in a non-reactive solvent preferably at room to reflux temperature for about two to three days. In the thiourea reaction, ethanol is the preferred solvent and the product is usually isolated as the isothiuronium hydrohalide salt which is formed directly. In the 5-mercaptotetrazole reaction, the preferred solvent is dimethylformamide and an acid scavenger, such as an alkali metal carbonate, is preferably included in the reaction.

Especially in the instances where $R_5$ and/or $R_6$ are other than hydrogen, compounds of Formula I may be prepared by the reaction of a compound of Formula V'

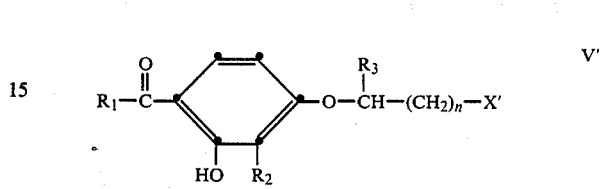

with an alkane formula VII

wherein $R_1$, $R_2$, $R_3$, $R_5$, $R_6$, X', and n are the same as previously defined and $R'_{10}$ is cyano (—CN) or a carboxylic ester, to give a compound of the Formula I"

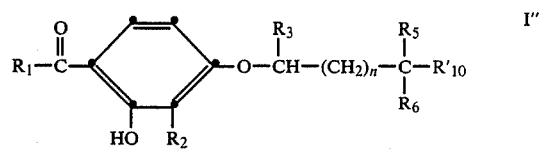

which can then be transformed into the compounds of this invention by the methods previously described. The reaction of compounds V' and VII is performed by first preparing the anion of compound VII by treating VII with a strong base, such as sodium metal dissolved in liquid ammonia with a catalytic amount of ferric chloride, sodium hydride or diisopropyl lithium amide in solvents such as tetrahydrofuran or dimethylformamide, and the like. The anion thus formed is treated with the intermediate V' (preferably where X' is bromo) which gives I".

Alternatively, I" may be prepared by first reacting the anion of VII with compound IV'

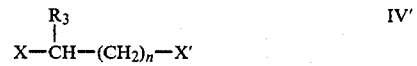

where n, $R_3$, X, and X' are the same as previously defined, and, where IV' is unsymmetrical, X' is a better leaving group than X, preferably bromo, to give intermediate III'

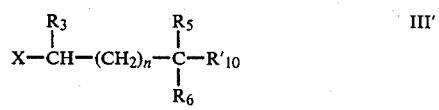

which can then be condensed with phenol II and transformed in the usual manner.

The thiotetrazole derivatives of this invention (p is 0) may be transformed into the corresponding sulfoxide (p is 1) compounds upon treatment with a mild oxidizing agent, such as hydrogen peroxide in methanol or an alkali metal periodate in aqueous alcohol. The corresponding sulfones (p is 2) are prepared from the thio or sulfoxide compounds on treatment with a strong oxidizing agent such as hydrogen peroxide in acetic acid or m-chloroperbenzoic acid in methanol.

When R is hydrogen, the tetrazole and thiotetrazole moieties exist in equilibrium between the 1H and 2H tautomers. To provide compounds where R is other than hydrogen, the 5-tetrazole and 5-thiotetrazole compounds may be alkylated with the appropriate alkyl halide or alkyl haloacetate to give both the 1- and 2-substituted 5-tetrazole and 5-thiotetrazole compounds which may be separated by such methods as chromatography or crystallization. Compounds where R is —CH$_2$COOH may be prepared from the corresponding esters by hydrolysis in the usual manner.

Intermediate compounds II, III, IV, IV', VI and VII are either commercially available, known in the literature, or can be prepared according to methods known in the art.

The following preparations and examples further illustrate the preparation of the starting materials, intermediates, and compounds of this invention. The examples are illustrative only and are not intended to limit the scope of the invention. The term "m/e" used in characterizing the products refers to the mass-to-charge ratio of ions which appear in the mass spectra of the products. In general, the values correspond to molecular weights of the major peaks, and are so designated "M+". Where structures were confirmed by infra-red or proton nuclear magnetic resonance analysis, the compound is so designated by "IR" and/or "NMR", respectively.

EXAMPLE 1

4-(4-Acetyl-3-hydroxy-2-propylphenoxy)butane nitrile

A. Preparation of 4-(4-acetyl-3-hydroxy-2-propylphenoxy)butyl bromide

A solution of 50 g. (257 mmoles) of 2,4-dihydroxy-3-propylacetophenone in 300 ml. of acetone was slowly dripped into a refluxing solution of 221.98 g. (1.028 moles) of 1,4-dibromobutane, 35.52 g. (257 mmoles) of potassium carbonate, and 4.5 g. of potassium iodide in 800 ml. of acetone over a period of 3 hours. The solution was allowed to reflux for about 19 hours. The solution was filtered warm and the filtrate was evaporated in vacuo. Distillation of the resulting yellow oil at 0.25 mm. of Hg resulted in the recovery of the excess dibromobutane (at about 30° C.) and 66.12 grams of the desired 4-(4-acetyl-3-hydroxy-2-propylphenoxy)butyl bromide at 180° C.

B. Preparation 4-(4acetyl-3-hydroxy-2-propylphenoxy)butane nitrile.

A solution of 30.0 g. (91.1 mmoles) of 4-(4-acetyl-3-hydroxy-2-propylphenoxy)butyl bromide and 4.91 g. (100.2 mmoles) of sodium cyanide in 225 ml. of dimethylformamide was heated to 75°–85° C. for about 17 hours. The reaction mixture was cooled to room temperature, filtered, and evaporated in vacuo at 75° C. Cold 0.1N hydrochloric acid was added to the residue, and the residue was extracted into ethyl acetate. The ethyl acetate layer was twice washed with 0.1N hydrochloric acid, dried over sodium sulfate, and evaporated in vacuo to yield 21.02 g. of 4-(4-acetyl-3-hydroxy-2-propylphenoxy)butane nitrile as a dark amber oil which crystallized as it cooled.

Analysis: C$_{16}$H$_{21}$NO$_3$; Calc.: C, 69.79; H, 7.69; N, 5.09; Found: C, 69.49; H, 7.42; N, 5.20.

EXAMPLES 2–7

The following nitrile intermediates were prepared according to the procedure in Example 1 using the appropriate dibromoalkane. The compounds were all oils which were used in subsequent transformations without further purification. Yields are expressed as the percent molar yield from the bromide intermediate.

2. 6-(4-Acetyl-3-hydroxy-2-propylphenoxy)hexane nitrile, 98% yield.

Analysis: C$_{18}$H$_{25}$NO$_3$; Calc.: C, 71.26; H, 8.31; N, 4.62; Found: C, 71.03; H, 8.04; N, 4.69.

3. 7-(4-Acetyl-3-hydroxy-2-propylphenoxy)-heptane nitrile, 83% yield.

Analysis: C$_{19}$H$_{27}$NO$_3$; Calc.: C, 71.89; H, 8.57; N, 4.41; Found: C, 72.16; H, 8.71; N, 4.69.

4. 8-(4-Acetyl-3-hydroxy-2-propylphenoxy)-octane nitrile, 86% yield.

Analysis: C$_{20}$H$_{29}$NO$_3$; Calc.: C, 72.47; H, 8.82; N, 4.23; Found: C, 70.97; H, 8.89; N, 4.21.

5. 9-(4-Acetyl-3-hydroxy-2-propylphenoxy)-nonane nitrile, ca. 100% yield.

Analysis: C$_{21}$H$_{31}$NO$_3$; Calc.: C, 73.01; H, 9.04; N, 4.05; Found: C, 72.75; H, 8.99; N, 4.01.

6. 10-(4-Acetyl-3-hydroxy-2-propylphenoxy)-decane nitrile, ca. 100% yield.

Analysis C$_{22}$H$_{33}$NO$_3$; Calc.: C, 73.50; H, 9.25; N, 3.90; Found: C, 64.48; H, 9.19; N, 2.97.

7. 12-(4-Acetyl-3-hydroxy-2-propylphenoxy)-dodecane nitrile, 95% yield.

Analysis: C$_{24}$H$_{37}$NO$_3$; Calc.: C, 74.38; H, 9.62; N, 3.61; Found: C, 74.16; H, 9.41; N, 3.41.

EXAMPLE 8

5-[4-(4-Acetyl-3-hydroxy-2-propylphenoxy)-butyl]-tetrazole

A solution of 20.73 g. (75 mmoles) of 4-(4-acetyl-3-hydroxy-2-propylphenoxy)butane nitrile, 14.63 g. (225 mmoles) of sodium azide, and 12.04 g. (225 mmoles) of ammonium chloride in 200 ml. of dimethylforamide was heated at 125° C. for about 17 hours. At this time an additional 9.75 g. (150 mmoles) of sodium azide and 8.02 g. (150 mmoles) of ammonium chloride were added and the heating was continued for an additional 6 hours. The reaction mixture was filtered hot and evaporated to dryness in vacuo yielding a viscous dark oil. The residue was treated with dilute hydrochloric acid and extracted with ethyl acetate. The ethyl acetate layer was dried over sodium sulfate and evaporated in vacuo yielding an oil which crystallized upon cooling. The crystals were boiled with decolorizing carbon in ethyl acetate for about 30 minutes. The solution was filtered hot, and the filtrate was cooled in the refrigerator to yield orange-amber crystals. The crystals were collected by vacuum filtration and washed with ethyl acetate to give 6.49 g. of the title product, m.p. about 113.5°–115° C.

Analysis: C$_{16}$H$_{22}$N$_4$O$_3$; Calc.: C, 60.36; H, 6.97; N, 17.60; O, 15.08; Found: C, 60.14; H, 6.86; N, 17.75; O, 15.12.

Examples 9–14

The following tetrazole compounds were prepared from the respective nitrile intermediates following the procedure of Example 8. Yields are expressed as the molar percent yield from the nitrile intermediate.

9. 5-[6-(4-Acetyl-3-hydroxy-2-propylphenoxy)-hexyl]-tetrazole, m.p. about 86.5°–90° C., 8% yield.
Analysis: $C_{18}H_{26}N_4O_3$; Calc.: C, 62.41; H, 7.57; N, 16.17; O, 13.85; Found: C, 62.17; H, 7.37; N, 16.41; O, 14.14.

10. 5-[7-(4-Acetyl-3-hydroxy-2-propylphenoxy)-heptyl]-tetrazole, m.p. about 92°–93.5° C., 35% yield.
Analysis: $C_{19}H_{28}N_4O_3$; Calc.: C, 63.31; H, 7.83; N, 15.54; Found: C, 63.54; H, 8.01; N, 15.70.

11. 5-[8-(4-Acetyl-3-hydroxy-2-propylphenoxy)-octyl]-tetrazole, m.p. about 82.5°–84.5° C., 4% yield.
Analysis: $C_{20}H_{30}N_4O_3$; Calc.: C, 64.15; H, 8.08; N, 14.96; O, 12.82;
Found: C, 64.12; H, 7.82; N, 15.06; O, 12.99.

12. 5-[9-(4-Acetyl-3-hydroxy-2-propylphenoxy)-nonyl]-tetrazole, m.p. about 107°–115° C., 68% yield.
Analysis: $C_{21}H_{32}N_4O_3$; Calc.: C, 64.92; H, 8.30; N, 14.42; O, 12.35; Found: C, 64.66; H, 8.49; N, 14.15; O, 12.61.

13. 5-[10-(4-Acetyl-3-hydroxy-2-propylphenoxy)-decyl]-tetrazole, m.p. about 74.5°–84.5° C., 18% yield.
Analysis: $C_{22}H_{34}N_4O_3$;
Calc.: C, 65.64; H, 8.51; N, 13.92; O, 11.92; Found: C, 65.59; H, 8.47; N, 14.11; O, 11.67.

14. 5-[12-(4-Acetyl-3-hydroxy-2-propylphenoxy)-dodecyl]-tetrazole, m.p. about 84°–88° C., 51% yield.
Analysis: $C_{24}H_{38}N_4O_3$; Calc.: C, 66.95; H, 8.90; N, 13.01; Found: C, 67.13; H, 8.77; N, 13.13.

EXAMPLE 15

6-(4-Acetyl-3-hydroxy-2-propylphenoxy)-6-(4-benzylphenyl)hexanoic acid

A. Preparation of adipic acid monomethylester monoacid chloride

One hundred grams of adipic acid monomethylester and 200 ml. of thionyl chloride were added to 300 ml. of methylene chloride followed by the addition of 1 ml. of dimethylformamide. The reaction was stirred at reflux for about 16 hours. After cooling, the reaction mixture was evaporated in vacuo. The resulting orange oil was vacuum distilled at 5 mm. of Hg. The distillate was collected from 97°–100° C. with most of the distillate coming at 98.5° C. A total of 95.7 g. of a light orange oil were collected and identified as adipic acid monomethyl ester monoacid chloride by NMR.

B. Preparation of methyl 6-(4-benzylphenyl)-6-oxo-hexanoate

A solution of 45.8 g. of adipic acid monomethylester monoacid chloride and 40.0 g. of diphenylmethane in 1000 ml. of methylene chloride was cooled to about −10° C. using an external ice/ethanol bath. Aluminum chloride (66.5 g.) was added over a two hour period keeping the temperature between −8° and −10° C. The reaction mixture was then added to a slush of hydrochloric acid in ice (total volume of 4000 ml.). The methylene chloride layer was separated and evaporated in vacuo leaving a light peach-colored viscous liquid which began to crystallize as it cooled. The material was vacuum distilled at 0.5 mm. of Hg from about 190° to 235° C. giving 34.7 g. of methyl 6-(4-benzylphenyl)-6-oxo-hexanoate.

C. Preparation of ethyl 6-(4-benzylphenyl)-6-hydroxy-hexanoate.

A solution of 34.7 g. of methyl 6-(4-benzylphenyl)-6-oxo-hexanoate in 300 ml. of ethanol was treated with 5.1 g. of sodium borohydride and the reaction mixture stirred for about 17 hours. The ethanol was removed by evaporating in vacuo. The residue was treated with cold dilute hydrochloric acid and was then extracted twice with ethyl acetate. The combined ethyl acetate layers were washed with water, dried over sodium sulfate, and evaporated in vacuo giving 26.6 g. of ethyl 6-(4-benzylphenyl)-6-hydroxyhexanoate as a yellow oil which was used in the subsequent reaction without further purification.

D. Preparation of ethyl 6-(4-benzylphenyl)-6-bromo-hexanoate

A solution of 25.3 g. of phosphorous tribromide in 100 ml. of methylene chloride was added to a solution of 26.6 g. of ethyl 6-(4-benzylphenyl)-6-hydroxy-hexanoate in 400 ml. of methylene chloride that had previously been chilled to −10° C. The reaction was stirred for about 16 hours allowing the reaction to come to room temperature. The reaction was added to 6 liters of ice water which was then extracted with ethyl acetate. The organic layer was washed with water, dried over sodium sulfate, and evaporated in vacuo giving 26.1 g. of ethyl 6-(4-benzylphenyl)-6-bromo-hexanoate as a yellow oil.

E. Preparation of ethyl 6-(4-acetyl-3-hydroxy-2-propylphenoxy)-6-(4-benzylphenyl)hexanoate A solution of 9.75 g. of ethyl 6-(4-benzylphenyl)-6-bromo-hexanoate, 5.03 g. of 2,4-dihydroxy-3-propylacetophenone, 3.57 g. of potassium carbonate, and 1.0 g. of potassium iodide in 175 ml. of acetone was heated to reflux for about 86 hours. The reaction was evaporated in vacuo and the residue was purified by chromatography over silica gel eluting with a 0–20% ethyl acetate gradient in hexane. The appropriate fractions were pooled and evaporated, giving 2.5 g. of the desired product which was used for the subsequent hydrolysis. NMR was consistent with the compound ethyl 6-(4-acetyl-3-hydroxy-2-propylphenoxy)-6-(4-benzylphenyl)hexanoate.

F. Preparation of 6-(4-acetyl-3-hydroxy-2-propylphenoxy)-6-(4-benzylphenyl)hexanoic acid A solution of 2.5 g. of ethyl 6-(4-acetyl-3-hydroxy-2-propylphenoxy)-6-(4-benzylphenyl)hexanoate in 40 ml. of 1N sodium hydroxide and 20 ml. of ethanol was stirred for 24 hours. The reaction was diluted with 100 ml. of water, and was extracted with hexane and ethyl acetate. The aqueous layer was acidified with hydrochloric acid and extracted twice with ethyl acetate. The ethyl acetate layers were combined, dried over sodium sulfate, and evaporated in vacuo yielding 1.83 g. of the title product.
Analysis: $C_{30}H_{34}O_5$; Calc.: C, 75.92; H, 7.22; Found: C, 75.65; H, 7.31.

EXAMPLE 16

6-(4-Acetyl-3-hydroxyphenoxy)-6-(4-benzylphenyl)-hexanoic acid

Following the procedure of Example 15, 3.75 g. of ethyl 6-(4-benzylphenyl)-6-bromo-hexanoate and 1.94 g. of 2,4-dihydroxyacetophenone were reacted to provide the intermediate ethyl hexanoate derivative which was then hydrolyzed to provide 0.95 g. of the title product as an oil.

Analysis: $C_{27}H_{28}O_5$; Calc.: C, 74.98; H, 6.53; Found: C, 74.75; H, 6.72.

EXAMPLE 17

6-(4-Acetyl-3-hydroxy-2-propylphenoxy)-6-(4-biphenyl)hexanoic acid

Following the procedure of Example 15, using biphenyl in place of diphenylmethane, the title product was prepared as an oil.

Analysis: $C_{29}H_{32}O_5$; Calc.: C, 75.63; H, 7.00; Found: C, 75.39; H, 7.17.

EXAMPLE 18

6-(4-Acetyl-3-hydroxyphenoxy)-6-(4-biphenyl)hexanoic acid

Following the procedure of Example 17, using 2,4-dihydroxyacetophenone in place of 2,4-dihydroxy-3-propylacetophenone, the title compound was prepared, m.p. about 66°-68° C.

Analysis: $C_{26}H_{26}O_5$; Calc.: C, 74.62; H, 6.26; Found: C, 74.82; H, 6.21.

EXAMPLE 19

6-(4-Acetyl-3-hydroxy-2-propylphenoxy)-6-phenylhexanoic acid

Following the procedure of Example 15 using benzene in place of diphenylmethane, the title product was prepared as an oil.

Analysis: $C_{23}H_{28}O_5$; Calc.: C, 71.85; H, 7.34; Found: C, 71.59; H, 7.25.

EXAMPLE 20

6-(4-Acetyl-3-hydroxyphenoxy)-6-phenylhexanoic acid

Following the procedure of Example 19, using 2,4-dihydroxyacetophenone in place of 2,4-dihydroxy-3-propylacetophenone, the title product was prepared, m.p. about 91°-93° C.

Analysis: $C_{20}H_{22}O_5$; Calc.: C, 70.16; H, 6.48; Found: C, 70.00; H, 6.32.

EXAMPLE 21

5-(4-Acetyl-3-hydroxy-2-propylphenoxy)pentane nitrile

A solution of 44.4 g. of 2,4-dihydroxy-3-propylacetophenone, 42.2 g. of 6-chlorocapronitrile, 33.2 g. of potassium carbonate and 4.0 g. of potassium iodide in one liter of methyl ethyl ketone was allowed to reflux for three days. The reaction mixture was filtered and the filtrate was evaporated in vacuo. Chromatography of the residue over silica gel (0–30% ethyl acetate gradient in hexane) gave 53.6 g. of the title product as an oil.

Analysis: $C_{17}H_{23}NO_3$; Calc.: C, 70.56; H, 8.01; N, 4.84; Found: C, 70.34; H, 8.22; N, 5.13.

EXAMPLE 22

5-[5-(4-Acetyl-3-hydroxy-2-propylphenoxy)pentyl]-tetrazole

Following the procedure of Example 8, 19.95 g. of 5-(4-acetyl-3-hydroxy-2-propylphenoxy)pentane nitrile were transformed into 12.7 g. of the title product, m.p. about 95°-96° C.

Analysis: $C_{17}H_{24}N_4O_3$; Calc.: C, 61.43; H, 7.28; N, 16.86; Found: C, 61.34; H, 7.08; N, 16.72.

EXAMPLE 23

5-[3-(4-Acetyl-3-hydroxy-2-propylphenoxy)-propyl]-tetrazole

The nitrile intermediate of the title compound was prepared following the procedure of Example 21 using 50.0 g. (257 mmoles) of 2,4-dihydroxy-3-propylacetophenone, 29.27 g. (282 mmoles) of 4-chlorobutyronitrile, 38.97 g. (282 mmoles) of potassium carbonate, and 4 g. of potassium iodide in 800 ml. of methyl ethyl ketone giving 57.58 g. of the nitrile intermediate as a rose-colored semi-crystalline solid. Twenty grams of the nitrile intermediate were then converted to the tetrazole in the usual manner giving 6.9 g. of the title compound, m.p. about 143°-145° C.

Analysis $C_{15}H_{20}N_4O_3$; Calc.: C, 59.20; H, 6.62; N, 18.41; Found: C, 58.96; H, 6.48; N, 18.49.

EXAMPLE 24

6-(4-Acetyl-3-hydroxy-2-propylphenoxy)-hexanoic acid

The benzhydryl ester of 6-bromohexanoic acid was prepared in situ by reacting 14.6 g. (80 mmoles) of 6-bromohexanoic acid with 17.0 g. (88 mmoles) of diphenyldiazomethane in 200 ml. methylene chloride with a catalytic amount of boron trifluoride etherate. The methylene chloride was removed by evaporating in vacuo and the resulting oil was dissolved in 300 ml. of methyl ethyl ketone. To the resulting solution was added 15.5 g. (80 mmoles) of 2,4-dihydroxy-3-propylacetophenone, 11.0 g. (80 mmoles) of potassium carbonate, and 2 g. of potassium iodide. The reaction was allowed to reflux overnight. The reaction was then filtered, and the solvent removed in vacuo. The resulting oil was dissolved in 200 ml. of ethyl acetate and approximately 50 ml. of hexane was added. This organic solution was washed 3 times each with 250 ml. of dilute potassium carbonate solution. The organic phase was dried over sodium sulfate, filtered, and the solvent evaporated in vacuo. The product was purified by high pressure liquid chromatography (silica gel/0–20% ethyl acetate gradient in hexane) which after crystallization from hexane/ethyl acetate afforded 24.9 g. of diphenylmethyl 6-(4-acetyl-3-hydroxy-2-propylphenoxy)-hexanoate.

Twenty grams of this benzhydryl ester were hydrolyzed by stirring in 150 ml. of formic acid and 10 ml. of triethylsilane for 2 days. The solvent was removed in vacuo and the residue taken up into ethyl acetate/hexane. The organic solution was then extracted with 200 ml. of dilute potassium carbonate solution. The aqueous solution was then acidified with dilute hydrochloric acid and extracted with 200 ml. of ethyl acetate. The ethyl acetate solution was dried over sodium sulfate, filtered, and evaporated to dryness. The residue was crystallized from methylene chloride/hexane, giving 5.3 g. of the title product, m.p. about 63°–64° C.

Analysis: $C_{17}H_{24}O_5$; Calc.: C, 66.21; H, 7.85; Found: C, 65.95; H, 7.63.

EXAMPLES 25–34

Following the procedure of Example 24, the following alkanoic acid derivatives were prepared using the appropriate phenols and bromoalkanoic acids. Yields are the molar yields based on the bromoalkanoic acid.

25. 6-(4-Acetyl-3-hydroxyphenoxy)hexanoic acid, m.p. about 130°–131° C., 6% yield.

Analysis: $C_{14}H_{18}O_5$; Calc.: C, 63.15; H, 6.81; Found: C, 63.13; H, 6.92.

26. 6-(4-Acetyl-3-hydroxy-2-allylphenoxy)hexanoic acid, m.p. about 82°–83° C., 16% yield.

Analysis: $C_{17}H_{22}O_5$; Calc.: C, 66.65; H, 7.24; Found: C, 66.70; H, 7.02.

27. 4-(4-Acetyl-3-hydroxy-2-propylphenoxy)-butanoic acid, m.p. about 132°–134° C, 21% yield.

Analysis: $C_{15}H_{20}O_5$; Calc.: C, 64.27; H, 7.19; Found: C, 64.02; H, 7.27.

28. 5-(4-Acetyl-3-hydroxy-2-propylphenoxy)-pentanoic acid, m.p. about 99°–100° C., 1% yield.

Analysis: $C_{16}H_{22}O_5$; Calc.: C, 65.29; H, 7.53; Found: C, 65.16; H, 7.34.

29. 7-(4-Acetyl-3-hydroxy-2-propylphenoxy)-heptanoic acid, m.p. about 59°–60° C., 19% yield.

Analysis: $C_{18}H_{26}O_5$; Calc.: C, 67.06; H, 8.13; Found: C, 67.19; H, 7.93.

30. 8-(4-Acetyl-3-hydroxy-2-propylphenoxy)-octanoic acid, m.p. about 77°–78° C., 19% yield.

Analysis: $C_{19}H_{28}O_5$; Calc.: C, 67.83; H, 8.39; Found: C, 68.13; H, 8.40.

31. 9-(4-Acetyl-3-hydroxy-2-propylphenoxy)-nonanoic acid, m.p. about 42°–43° C., 24% yield.

Analysis: $C_{20}H_{30}O_5$; Calc.: C, 68.55; H, 8.63; Found: C, 68.69; H, 8.40.

32. 10-(4-Acetyl-3-hydroxy-2-propylphenoxy)-decanoic acid, m.p. about 55°–56° C., 26% yield. Analysis: $C_{21}H_{32}O_5$; Calc.: C, 69.20; H, 8.85; Found: C, 69.54; H, 8.73.

33. 11-(4-Acetyl-3-hydroxy-2-propylphenoxy)-undecanoic acid, m.p. about 58°–59° C., 17% yield.

Analysis: $C_{22}H_{34}O_5$; Calc.: C, 69.81; H, 9.05; Found: C, 69.93; H, 8.94.

34. 6-(4-Propionyl-3-hydroxy-2-propylphenoxy)-hexanoic acid, m.p. about 113°–114° C., 19% yield.

Analysis: $C_{18}H_{26}O_5$; Calc.: C, 67.06; H, 8.13; Found: C, 66.23; H, 8.73.

EXAMPLE 35

N-[6-(4-Acetyl-3-hydroxy-2-propylphenoxy)-hexyl]-morpholine hydrochloride

A solution of 10.7 g. (30 mmoles) of 6-(4-acetyl-3-hydroxy-2-propylphenoxy)hexyl bromide and 5.76 g. (66 mmoles) of morpholine in 100 ml. of dimethylformamide was stirred for 16 hours. The solvent was removed by evaporation and the residue was partitioned between 200 ml. of ethyl acetate and 200 ml. of dilute hydrochloric acid. The aqueous layer was separated and then made basic with dilute potassium carbonate solution. The solution was extracted with ethyl acetate, and the ethyl acetate layer was separated, dried over sodium sulfate, and evaporated to dryness. The residue was dissolved in 200 ml. of ether and gaseous hydrogen chloride was bubbled into the solution. The resulting precipitate was filtered to give 8.6 g. of the title product, m.p. about 157°–159° C.

Analysis: $C_{21}H_{33}NO_4 \cdot HCl$; Calc.: C, 63.02; H, 8.57; N, 3.50; Found: C, 62.82; H, 8.35; N, 3.42.

EXAMPLES 36–38

Following the procedure of Example 35, the following compounds were prepared using the appropriate amines.

36. 6-(4-Acetyl-3-hydroxy-2-propylphenoxy)-hexylamine hydrochloride, m.p. about 120°–121° C.

Analysis: $C_{17}H_{27}NO_3 \cdot HCl$; Calc.: C, 61.90; H, 8.56; N, 4.25; Found: C, 61.36; H, 7.44; N, 3.41.

37. N-Methyl-N'-[5-(4-acetyl-3-hydroxy-2-propylphenoxy)pentyl]piperazine dihydrochloride, m.p. about 215° C. (decomposition).

Analysis: $C_{22}H_{34}N_2O_3 \cdot 2HCl$; Calc.: C, 58.79; H, 8.52; N, 6.23; Found: C, 58.99; H, 8.72; N, 6.16.

38. N,N-Dimethyl-[6-(4-acetyl-3-hydroxy-2-propylphenoxy)hexyl]amine hydrochloride, m.p. about 110°–112° C.

Analysis: $C_{19}H_{31}NO_3 \cdot HCl$; Calc.: C, 63.76; H, 9.01; N, 3.91; Found: C, 63.54; H, 8.74; N, 4.13.

EXAMPLE 39

5-[5-(4-Acetyl-3-hydroxy-2-propylphenoxy)-1,1-dimethylpentyl]-tetrazole

A catalytic amount of ferric chloride was added to approximtely 200 ml. of ammonia, followed by 1.84 g. (80 mmoles) of sodium metal. A solution of 3.64 ml. of isobutyronitrile in 50 ml. of ether was added to the ammonia solution in a dropwise manner over period of 2 minutes. Five minutes after the addition was complete, a solution of 3.16 g. (40 mmoles) of 4-(4-acetyl-3-hydroxy-2-propylphenoxy)butyl bromide in 50 ml. of ether was added over a 2 minute period. The reaction was stirred for 16 hours during which time the ammonia evaporated. The product was partitioned between ethyl acetate and dilute hydrochloric acid. The ethyl acetate was evaporated and the residue was purified by high pressure liquid chromatography to afford 5.6 g. of 5-(4-acetyl-3-hydroxy-2-propylphenoxy)-1,1-dimethylpentyl nitrile.

Analysis: $C_{19}H_{27}NO_3$; Calc.: C, 71.89; H, 8.57; N, 4.41; Found: C, 72.14; H, 8.61; N, 4.19.

This nitrile intermediate (2.5 g.) was converted to the tetrazole according to the procedure of Example 8 to give 0.2 g. of the title compound, m.p. about 112°–115° C.

Analysis: $C_{19}H_{28}N_4O_3$; Calc.: C, 63.31; H, 7.83; N, 15.54; Found: C, 63.33; H, 8.08; N, 15.75.

EXAMPLE 40

6-(4-Acetyl-3-hydroxy-2-propylphenoxy)heptanoic acid

Following the procedure of Example 15, ethyl 6-oxoheptanoate was transformed into ethyl 6-bromoheptanoate. The reaction of 4.74 g. of ethyl 6bromoheptanoate and 3.88 g. of 2,4-dihydroxy-3-propylacetophenone followed by hydrolysis in the usual manner gave 300 mg. of the title product as an oil.

Analysis: $C_{18}H_{26}O_5$; Calc.: C, 67.06; H, 8.13; Found: C, 66.03; H, 7.76.

EXAMPLE 41

6-(4-Acetyl-3-hydroxyphenoxy)heptanoic acid

Following the procedure of Example 40, 4.74 g. of ethyl 6-bromoheptanoate and 3.04 g. of 2,4-dihydroxyacetophenone were reacted in the usual manner and the resulting product hydrolyzed to give the title product, m.p. about 116°–118° C.

Analysis: $C_{15}H_{20}O_5$; Calc.: C, 64.27; H, 7.19; Found: C, 64.15; H, 7.38.

EXAMPLE 42

6-(4-Acetyl-3-hydroxy-2-propylphenoxy)-1-hexanol

A solution of 10 g. of 2,4-dihydroxy-3-propylacetophenone, 8 g. of potassium carbonate, and 7.1 g. of 6-chloro-1-hexanol in 50 ml. of methyl ethyl ketone was heated to reflux overnight. Upon cooling, dilute hydrochloric acid was added and the resulting organic layer was separated, dried over sodium sulfate, and evaporated to dryness. The residue was purified by chromatography giving 2.87 g. of the title product as an oily solid.

Analysis: $C_{17}H_{26}O_4$; Calc.: C, 69.36; H, 8.90; Found: C, 69.09; H, 8.56.

EXAMPLE 43

5-[4-(4-Benzoyl-3-hydroxy-2-propylphenoxy)butyl]-tetrazole

The title compound was prepared by first reacting 7.68 g. of 2,4-dihydroxy-3-propylbenzophenone with 4.86 g. of 5-bromovaleronitrile according to the procedure in Example 21. The reaction afforded 8.2 g. of the nitrile intermediate of the title compound. This nitrile intermediate was then converted to the tetrazole following the procedure of Example 8 giving 1.2 g. of the title compound, m.p. about 114–°115° C.

Analysis: $C_{21}H_{24}N_4O_3$; Calc.: C, 66.30; H, 6.36; Found: C, 66.15; H, 6.36.

EXAMPLE 44

Methyl 6-(4-acetyl-3-hydroxy-2-propylphenoxy)-2,2-dimethylhexanoate

A. Preparation of methyl 6-bromo-2,2-dimethylhexanoate.

To a solution of 5.0 g. of dry diisopropylamine in 60 ml. of dry tetrahydrofuran at −70° C. were added dropwise via a syringe 32.6 ml. of a 1.5M solution of n-butyllithium in hexane. After stirring for about 20 minutes at −70° C., 6.0 g. of methyl isobutyrate were added and the reaction mixture allowed to stir at −70° C. for about 40 minutes. A solution of 15.76 g. of 1,4-dibromobutane in a small volume of tetrahydrofuran was then added to the reaction mixture. The reaction mixture was slowly brought to room temperature over a period of about three hours. The reaction was quenched with 2.5 ml. of methanol. Fifty ml. of methylene chloride were added followed by the addition of 50 ml. of 0.5N sodium hydroxide. The layers were separated and the aqueous phase was extracted with 50 ml. of methylene chloride. The combined organic layers were washed once with water, once with a saturated sodium chloride solution, dried over sodium sulfate, and concentrated in vacuo to give 14 g. of a pale yellow liquid, which was identified as methyl 6-bromo-2,2-dimethylhexanoate by NMR and IR.

B. Preparation of methyl 6-(4-acetyl-3-hydroxy-2-propylphenoxy)-2,2-dimethylhexanoate.

Following the procedure of Example 15, 2.5 g. of methyl 6-bromo-2,2-dimethylhexanoate, 1.46 g. of potassium carbonate, a catalytic amount of potassium iodide, and 2.14 g. of 2,4-dihydroxy-3-propylacetophenone were reacted to give 2.96 g. of the title product as a brown oil. IR, NMR.

EXAMPLE 45

6-(4-Acetyl-3-hydroxy-2-propylphenoxy)-2,2-dimethylhexanoic acid

A solution of 1.1 g. of methyl 6-(4-acetyl-3-hydroxy-2-propylphenoxy)-2,2-dimethylhexanoate and 2.6 g. of lithium iodide in 50 ml. of collidine was heated to 100° C. under a nitrogen blanket for about 46 hours. The reaction mixture was then added to ice. After making the solution acidic with hydrochloric acid, the solution was extracted with ether. The ether phase was washed three times with a 10% sodium bicarbonate solution. The ether solution was then further washed with a dilute hydrochloric acid solution, water, and a saturated sodium chloride solution. Evaporating the ether layer to dryness gave 1.03 g. of the title product, $M^+=336$; NMR.

EXAMPLE 46

Methyl 6-(4-acetyl-3-hydroxyphenoxy)-2,2-ethylhexanoate

Following the procedure of Example 44, 2.5 g. of methyl 6-bromo-2,2-dimethylhexanoate, 1.46 g. of potassium carbonate, a catalytic amount of potassium iodide, and 1.67 g. of 2,4-dihydroxyacetophenone were reacted in 125 ml. of acetone giving 2.3 g. of the title product as an oil. $M^+=308$; NMR.

EXAMPLE 47

6-(4-Acetyl-3-hydroxyphenoxy)-2,2-dimethylhexanoic acid

Following the procedure of Example 45, 1.0 g. of methyl 6-(4-acetyl-3-hydroxphenoxy)-2,2-dimethyl hexanoate was hydrolyzed to give 0.86 g. of the title product. $M^+=294$; NMR.

EXAMPLE 48

6-(4-Acetyl-3-hydroxy-2-propylphenoxy)-nonanoic acid Following the procedures of Examples 15E and F, 1.18 g. of methyl 6-bromo-nonanoate and 0.91 g. of 2,4-dihydroxy-3-propylacetophenone were reacted in the presence of 0.65 g. of potassium carbonate in 40 ml. of acetone. Hydrolysis of the ester intermediate with sodium hydroxide in aqueous ethanol gave the title product $M^+=350$; NMR.

EXAMPLE 49

6-(4-Acetyl-3-hydroxyphenoxy)nonanoic acid

Following the procedure of Example 48, 1.13 g. of methyl 6-bromo-nonanoate and 1.31 g. of 2,4-dihydroxyacetophnone were reacted in 50 ml. of methyl ethyl ketone. Hydrolysis of the resulting methyl ester intermediate gave 0.3 g. of the title product, $M+308$; NMR, IR.

EXAMPLES 50-51

5-(1H)-[5-(4-Acetyl-3-hydroxy-2-propylphenoxy)pentyl]-1-tetrazolylacetic acid and
5-(2H)-[5-(4-acetyl-3-hydroxy-2-propylphenoxy)pentyl]-2-tetrazolyl acid A solution of 3.32 g. of 5-[5-(4-acetyl-3-hydroxy-2-propylphenoxy)pentyl]-tetrazole, 1.38 g. of potassium carbonate, 0.5 g. of potassium iodide, and 1.67 g. of ethyl bromoacetate in 100 ml. of methyl ethyl ketone was allowed to reflux for 24 hours. The solvent was removed by evaporation and the residue was dissolved in 250 ml. of ethyl acetate. The solution with 200 ml. of a saturated potassium carbonate solution. The organic layer was evaporated to dryness and the residue was purified by chromatography over silica gel. Eight-tenths of a gram of a faster eluting material were recovered and characterized as ethyl ester of the 2-substituted tetrazole product. The later eluting material weighed 1.0 g. and was characterized as the ethyl ester of the 1-substituted isomer. Each of the ester isomers was individually hydrolyzed according to the procedure of Example 15F giving the following products:

5-(1H)-[5-(4-acetyl-3-hydroxy-2-propylphenoxy)pentyl]-1-tetrazolylacetic acid, 600 mg., m.p. about 148°–149° C.

Analysis: $C_{19}H_{26}N_4O_5$; Calc.: C, 58.45; H, 6.71; N, 14.35; Found: C, 58.22; H, 7.00; N, 14.14.

5-(2H)-[5-(4-acetyl-3-hydroxy-2-propylphenoxy)pentyl]-2-tetrazolylacetic acid, 500 mg., m.p. about 99-°100° C.

Analysis: $C_{19}H_{26}N_4O_5$; Calc.: C, 58.45; H, 6.71; N, 14.35; Found: C, 58.18; H, 6.74; N, 14.13.

EXAMPLE 52

1-Methyl-5-(1H)-[5-(4-acetyl-3-hydroxy-2-propylphenoxy)pentyl]-tetrazole

A solution of 5 g. of 5-[5-(4-acetyl-3-hydroxy-2-propylphenoxy)pentyl]-tetrazole, 3 g. of potassium carbonate, and 2.4 g. of methyl iodide in 250 ml. of methyl ethyl ketone was allowed to reflux overnight. The reaction mixture was treated with dilute hydrochloric acid and the layers were separated. The organic layer was dried over sodium sulfate and evaporated to dryness. The residue was purified by chromatography over silica gel (2% ethanol in methylene chloride). The appropriate fractions were pooled and evaporated to an oil. Crystallization from ethyl acetate/hexane afforded 1.5 g. of the title product, m.p. about 72°–75° C.

Analysis: $C_{18}H_{26}N_4O_3$; Calc.: C, 62.41; H, 7.57; N, 16.17; Found: C, 62.14; H, 7.40; N, 15.91.

EXAMPLE 53

Alternate preparation of 5-(4-acetyl-3-hydroxy-2-propylphenoxy)pentanoic acid

The title product was prepared by heating 15.0 g. of 4-(4-acetyl-3-hydroxy-2-propylphenoxy)butane nitrile to reflux for six hours in 300 ml. of 2B ethanol and 40 ml. of 25% aqueous sodium hydroxide. The solution was evaporated to dryness and the residue was partitioned between diethyl ether and dilute sodium hydroxide solution. The aqueous layer was separated and acidified. The aqueous layer was extracted with ether. The ether extract was dried over sodium sulfate and evaporated to dryness. The residue was triturated with hexane and filtered to give 11 g. of the title product.

EXAMPLE 54

Ethyl 5-(4-acetyl-3-hydroxy-2-propylphenoxy)-pentanoate

Eleven grams of 5-(4-acetyl-3-hydroxy-2-propylphenoxy)pentanoic acid were dissolved in 200 ml. of absolute ethanol. With stirring, 1 ml. of sulfuric acid was added and the reaction was stirred overnight. The solvent was evaporated in vacuo and the residue partitioned between ethyl acetate and dilute potassium carbonate solution. The ethyl acetate was separated, dried, and evaporated to give 9.9 g. of the title product, $M^+ = 322$.

Analysis: $C_{18}H_{26}O_5$; Calc.: C, 67.06; H, 8.13; Found: C, 66.43; H, 7.03.

EXAMPLE 55

5-(4-Acetyl-3-hydroxy-2-propylphenoxy)pentanoic acid amide

The acid chloride of 5-(4-acetyl-3-hydroxy-2-propylphenoxy)pentanoic acid was prepared by dissolving 9.3 g. of the acid in 150 ml. of methylene chloride followed by the addition of ten drops of dimethylformamide and 5.22 ml. of oxalyl chloride. After stirring at room temperature for one hour, the solvent was evaporated in vacuo. The residue was dissolved in benzene and evaporated in vacuo. The resulting acid chloride was dissolved in 100 ml. of methylene chloride and the solution was divided in half. One-half of the acid chloride solution was used in Example 56; the other half (50 ml.) of the acid chloride solution was added dropwise to 200 ml. of liquid ammonia. After stirring overnight, the solvent was evaporated and the residue was partitioned between dilute hydrochloric acid and ethyl acetate. The ethyl acetate solution was separated, washed once with dilute aqueous potassium carbonate, dried over sodium sulfate, filtered and evaporated to dryness. Crystallization from methylene chloride/hexane resulted in a total of 2.8 g. (two crops) of the title product, m.p. about 108°–110° C.

Analysis: $C_{16}H_{23}NO_4$; Calc.: C, 65.51; H, 7.90; N, 4.77; Found: C, 65.30; H, 7.70; N, 4.47.

EXAMPLE 56

N,N-diethyl-5-(4-acetyl-3-hydroxy-2-propylphenoxy)-pentanoic acid amide

The remaining 50 ml. of the methylene chloride/acid chloride solution from Example 55 were added to 50 g. of dimthylamine in 100 ml. of methylene chloride. The reaction was worked up in the same manner as Example 55. Crystallization of the product from methylene chloride/hexane afforded 2.1 g. of the title product, m.p. about 95°–97° C.

Analysis: $C_{18}H_{27}NO_4$; Calc.: C, 67.26; H, 8.47; N, 4.36; Found: C, 67.03; H, 8.23; N, 4.11.

EXAMPLE 57

5-[4-(4-Acetyl-3-hydroxy-2-propylphenoxy)butanethio]-tetrazole

A solution of 6.58 g. of 4-(4-acetyl-3-hydroxy-2-propylphenoxy)butyl bromide, 3.04 g. of potassium carbonate, and 2.02 g. of 5-mercaptotetrazole in 50 ml. of dimethylformamide was stirred for 2 days at room temperature. The reaction was evaporated to dryness in vacuo and the residue was dissolved in 150 ml. of ethyl acetate. The ethyl acetate was washed twice with 200 ml. each of dilute hydrochloric acid. The ethyl acetate solution was diluted with hexane to cloudiness and then extracted with 100 ml. of dilute potassium carbonate solution. The basic aqueous layer was then acidified with dilute hydrochloric acid and extracted with 250 ml. of ethyl acetate. The ethyl acetate layer was dried over sodium sulfate, filtered, and evaporated to dryness. The resulting residue was crystallized from methylene chloride/hexane to give 2.65 g. of the title product, m.p. about 80°–81° C.

Analysis: $C_{16}H_{22}N_4O_3S$; Calc.: C, 54.84; H, 6.33; N, 15.99; Found: C, 54.57; H, 6.12; N, 16.08.

EXAMPLE 58-59

Following the procedure of Example 57, the following compounds were prepared using the appropriate bromide intermediates.

58. 5-[2-(4-Acetyl-3-hydroxy-2-propylphenoxy)ethanethio]-tetrazole, m.p. about 121°–122° C.

Analysis: $C_{14}H_{18}N_4O_3S$; Calc.: C, 52.16; H, 5.63; N, 17.38; Found: C, 52.34; H, 5.11; N, 17.13.

59. 5-[3-(4-Acetyl-3-hydroxy-2-propylphenoxy)propanethio]-tetrazole, m.p. 129°–130° C.

Analysis: $C_{15}H_{20}N_4O_3S$; Calc.: C, 53.55; H, 5.99; N, 16.65; Found: C, 53.91; H, 5.96; N, 16.39.

EXAMPLE 60

S-[3-(4-Acetyl-3-hydroxy-2-propylphenoxy)propyl]-isothiuronium hydrobromide

A solution of 3.15 g. of 3-(4-acetyl-3-hydroxy-2-propylphenoxy)propyl bromide and 0.84 g. of thiourea in 100 ml. of ethanol was allowed to reflux for about three days. The solution was then evaporated in vacuo to a volume of about 50 ml. Diethyl ether was added until cloudy and the solution was placed in the freezer. A gum formed which was recovered by decantation. The mother liquor was again treated with ether to form a second gum. The mother liquor was evaporated to dryness. The two gums and the mother liquor residue were then each triturated with methylene chloride and the resulting residues were combined and crystallized from isopropanol/ether, to afford 0.8 g. of the title product, m.p. about 114°–115° C.

Analysis: $C_{15}H_{22}N_2O_3S \cdot HBr$; Calc.: C, 46.04; H, 5.92; N, 7.16; Br, Found: C, 47.95; H, 5.91; N, 6.85; Br, 20.80.

EXAMPLE 61

5-(4-Acetyl-3-hydroxy-2-propylphenoxy)pentanehydroxamic acid

Four and six-tenths grams of 5-(4-acetyl-3-hydroxy-2-propylphenoxy)pentanoic acid were converted to the corresponding acid chloride according to the procedure of Example 55. The resulting acid chloride and 1.05 g. of hydroxylamine hydrochloride were dissolved in 50 ml. of methylene chloride, after which were added 4.15 ml. of triethylamine in about 50 ml. of methylene chloride. After stirring overnight at room temperature, the methylene chloride was removed by evaporation and the residue was partitioned between ethyl acetate and dilute hydrochloric acid. The layers were separated, and the ethyl acetate solution was evaporated in vacuo. The residue was dissolved in diethyl ether and the solution was extracted with dilute sodium hydroxide solution. The aqueous basic solution was then made acidic with dilute hydrochloric acid and the solution was extracted with ethyl acetate. The ethyl acetate layer was dried over sodium sulfate and evaporated to dryness. The residue was crystallized from methylene chloride/hexane to provide 400 mg. of the title product.

Analysis: $C_{16}H_{23}NO_5$; Calc.: C, 62.12; H, 7.49; N, 4.53; Found: C, 62.05; H, 7.40; N, 4.70.

EXAMPLE 62

4-(4-Acetyl-3-hydroxy-2-propylpheoxy)butane thiocyanate

To 10.65 g. of 4-(4-acetyl-3-hydroxy-2-propylphenoxy)butyl bromide in 60 ml. of dry dimethylsulfoxide were added 6.5 g. of potassium thiocyanate. The solution was stirred overnight at room temperature and then was poured into water. The solution was extracted twice with dichloromethane. The combined organic extracts were washed with water, dried over magnesium sulfate, filtered, and evaporated in vacuo. The resulting oil was vacuum distilled to provide the title compound in 95% yield as a yellow viscous oil, b.p. about 205° C. at 0.45 torr.

Analysis: $C_{16}H_{21}NO_3S$; Calc.: C, 62.51; H, 6.89; N, 4.56; O, 15.61; S, 10.43; Found: C, 62.29; H, 6.61; N, 4.68; O, 15.71; S, 10.54.

EXAMPLES 63-67

Following the procedure of Example 62, the following thiocyanate intermediates were prepared from the corresponding bromide intermediates.

63. 3-(4-Acetyl-3-hydroxy-2-propylphenoxy)propane thiocyanate, b.p. about 210° C. at 0.25 torr, yield.

Analysis: $C_{15}H_{19}NO_3S$; Calc: C, 61.41; H, 6.53; N, 4.77; O, 16.36; S, 10.93; Found: C, 61.25; H, 6.50; N, 4.69; O, 16.33; S, 10.86.

64. 5-(4-Acetyl-3-hydroxy-2-propylphenoxy)pentane thiocyanate, b.p. about 210° C. at 0.6 torr, 92% yield.

Analysis: $C_{17}H_{23}NO_3S$; Calc: C, 63.52; H, 7.21; N, 4.36; O, 14.93; S, 9.98; Found: C, 63.40; H, 7.29; N, 4.28; O, 14.89; S, 9.90.

65. 6-(4-Acetyl-3-hydroxy-2-propylphenoxy)hexane thiocyanate, b.p. about 220° C. at 0.4 torr, 87% yield.

Analysis: $C_{18}H_{25}NO_3S$; Calc.: C, 64.44; H, 7.51; N, 4.18; O, 14.31; S, 9.56; Found: C, 64.31; H, 7.71; N, 4.00; O, 14.22; S, 9.36.

66. 7-(4-Acetyl-3-hydroxy-2-propylphenoxy)heptane thiocyanate, b.p. about 224° C. at 0.5 torr, 81% yield.

Analysis: $C_{19}H_{27}NO_3S$: Calc: C, 65.29; H, 7.79; N, 4.01; O, 13.73; S, 9.18; Found: C, 65.18; H, 8.07; N, 3.97; O, 13.79; S, 9.97.

67. 8-(4-Acetyl-3-hydroxy-2-propylphenoxy)octane thiocyanate, b.p. about 234° C. at 0.25 torr, 89% yield.

Analysis: $C_{20}H_{29}NO_3S$; Calc.: C, 66.08; H, 8.04, N, 3.85; O, 13.20; S, 8.82; Found: C, 65.86; H, 7.88; N, 3.67; O, 13.26; S, 8.63.

EXAMPLE 68

5-[5-(4-Acetyl-3-hydroxy-2-propylphenoxy)pentanethio]-tetrazole

To 5.8 g. (18 mmoles) of 5-(4-acetyl-3-hydroxy-2-propylphenoxy)pentane thiocyanate in 70 ml. of dry dimethylformamide were added 36 mmoles of ammonium chloride and 72 mmoles of sodium azide. The resulting suspension was heated overnight at about 80° C. After cooling, the solution was quenched with water and the resulting suspension was acidified with hydrochloric acid. The mixture was extracted three times with chloroform and the combined chloroform extracts were back-extracted with 20% aqueous sodium hydroxide. After washing the basic solution once with chloroform, the solution was acidified with hydrochloric acid. The resulting precipitate was collected by filtration and crystallized from methanol to give a 78% yield of the title product, m.p. about 96°–98° C.

Analysis: $C_{17}H_{24}N_4O_3S$; Calc.: C, 56.02; H, 6.64; N, 15.37; O, 13.17; S, 8.80; Found: C, 55.88; H, 6.89; N, 15.55; O, 13.00; S, 7.95.

EXAMPLES 69–73

Following the procedure of Example 68, the following products were prepared from the corresponding thiocyanate intermediates.

69. 5-[3-(4-Acetyl-3-hydroxy2-propylphenoxy)-propanethio]-tetrazole, m.p. about 131-133° C., 74% yield.

Analysis: $C_{15}H_{20}N_4O_3S$; Calc.: C, 53.55; H, 5.99; N, 16.66; O, 14.27; S, 9.53; Found: C, 53.33; H, 5.85; N, 16.36; O, 14.47; S, 9.23.

70. 5-[4-(4-Acetyl-3-hydroxy-2-propylphenoxy)-butanethio]-tetrazole, m.p. about 84°–86° C., 79% yield.

Analysis: $C_{16}H_{22}N_4O_3S$; Calc.: C, 54.84; H, 6.33; N, 15.99; O, 13.70; S, 9.15; Found: C, 54.63; H, 6.10; N, 15.96; O, 13.78; S, 8.85.

71. 5-[6-(4-Acetyl-3-hydroxy-2-propylphenoxy)hexanethio]-tetrazole, m.p. about 85°–87° C., 54% yield.

Analysis: $C_{18}H_{26}N_4O_3S$; Calc.: C, 57.12; H, 6.93; N, 14.81; O, 12.68; S, 8.47; Found: C, 56.89; H, 6.86; N, 14.64; O, 12.43; S, 8.22.

72. 5-[7-(4-Acetyl-3-hydroxy-2-propylphenoxy)heptanethio]-tetrazole, m.p. about 84°–86° C., 65% yield.

Analysis: $C_{19}H_{28}N_4O_3S$; Calc.: C, 58.14; H, 7.19; N, 14.28; O, 12.27; S, 8.17; Found: C, 57.89; H, 6.91; N, 14.33; O, 12.09; S, 8.09.

73. 5-[8-(4-Acetyl-3-hydroxy-2-propylphenoxy)octanethio]-tetrazole, m.p. about 66°–68° C., 38% yield.

Analysis: $C_{20}H_{30}N_4O_3S$; Calc.: C, 59.08; H, 7.44; N, 13.78; O, 11.81; S, 7.89; Found: C, 59.31; H, 7.51; N, 13.66; O, 11.61; S, 7.65.

EXAMPLE 74

5-[5-(4-Acetyl-3-hydroxy-2-propylphenoxy)pentanesulfonyl]-tetrazole

To a solution of 1.8 g. of 5-[5-(4-acetyl-3-hydroxy-2-propylphenoxy)pentanethio]-tetrazole in 20 ml. of glacial acetic acid were added 5 ml. of 30% hydrogen peroxide. The solution was heated at 60° C. for about five hours. The cooled solution was evaporated under reduced pressure, water was added, and the mixture was extracted with dichloromethane. The organi extract was dried over magnesium sulfate, filtered, and evaporated in vacuo to give the title product as a yellow oil.

The compounds of Formula I should be useful in treating any condition, including clinical conditions, which is characterized by excessive release of leukotrienes $C_4$, $D_4$, or $E_4$. These conditions include immediate type hypersensitivity reactions such as asthma. Evidence obtained over the past few years has shown the presence of leukotrienes in sputum of patients with chronic bronchitis (Turnbull, et al., Lancet II, 526 (1977)) and cystic fibrosis (Cromwell, et al., Lancet II, 164 (1981)), suggesting a role of leukotrenes in the pathology of those diseases. Furthermore, Lewis and colleagues [Int. J. Immunopharmacology, 4, 85 (1982)]have recently detected material in rheumatoid synovial fluid that reacts antigenically with antibody to $LTD_4$. This may hallmark the existence of leukotriene permeability factors that, together with $LTB_4$, augment the inflammatory process in the diseased joints. Therefore, the compounds described in this invention should also alleviate some of the symptoms of chronic bronchitis and cystic fibrosis and possibly rheumatoid arthritis by virtue of their ability to antagonize leukotrienes.

In addition, some of the compounds of Formula I have dmonstrated lipoxygenase activity which further suggests the use of these compounds as anti-inflammatory agents.

SRS-A or leukotriene antagonism was demonstrated by the following test procedure:

Male, Hartley guinea pigs weighing 200-450 grams were killed by decapitation. A section of terminal ileum was removed, the lumen cleaned, and the tissue divided into 2.5 cm. segments. The ilea were mounted in 10 ml. tissue baths containing Krebs-bicarbonate solution of the following composition in mmoles/liter: KCl, 4.6; $CaCl_2 \cdot 2H_2O$, 1.2; $KH_2PO_4$, 1.2; $MgSO_4 \cdot 7H_2O$, 1.2; NaCl, 118.2; $NaHCO_3$, 24.8 and dextrose, 10.0. The bath fluid was maintained at 37° C. and aerated with 95 percent oxygen and 5 percent $CO_2$. In addition, the buffer contained $1 \times 10^{-6}M$ atropine to reduce ileal spontaneous activity. In studies with crude SRS-A, $1 \times 10^{-6}M$ pyrilamine was used to mitigate the actions of histamine present along with the biologically active leukotrienes. Isometric measurements were made with a Grass FTO3C force-displacement transducer and recorded on a Grass polygraph as change in grams of force. A passive force of 0.5 g. was applied to the tissues. After an appropriate equilibration period, single submaxial control responses to either SRS-A or pure $LTD_4$ were obtained. Following a 5 minute exposure of the ileum to an experimental drug, the control concentration of SRS-A or $LTD_4$ was added to the tissue bath. The response of the ileum to SRS-A or $LTD_4$ in the presence of the drug was compared to the response in the absence of the drug.

For some of the drugs in this series a more detailed analysis of $LTD_4$ antagonism was made. In these experients, cumulative concentration-response curves were obtained to $LTD_4$ in guinea pig ileum and trachea. This was followed by a 30 minute incubation with various concentrations of the experimental drug. The concentration response curve to $LTD_4$ was then repeated in the presence of the antagonist. Only one concentration of antagonist was used on a single tissue. $K_B$ values were calculated by the method of Furchgott [Ann. N.Y. Acad. Sci., 139, 553 (1967)]using the following equation.

$$K_B = \frac{[\text{Antagonist}]}{\text{Dose Ratio} - 1}$$

Dose ratio refers to the concentration of agonist required to elicit 50 percent of the maximal response in the presence of the antagonist divided by the ($ED_{50}$)in the absence of the antagonist. Calculations were performed with the aid of a computer and a digital plotter. The compounds of Formula I showed varying degrees of leukotriene antagonist activity when assayed on the isolated guinea pig ileum a summarized in Table I:

TABLE 1

| Compound of Example No. | Percent Inhibition of LTD$_4$ or SRS-A* evoked ileal contractions | | | |
|---|---|---|---|---|
| | Compound concentration | | | |
| | $1 \times 10^{-5}$ M | $3 \times 10^{-6}$ M | $1 \times 10^{-6}$ M | $pA_2$ |
| 8 | | 100 | 89 | 7.2 |
| 9 | | 100 | 87 | 7.1 |
| 10 | | 95 | 92 | 7.1 |
| 11 | | 100 | 89 | 6.5 |
| 12 | | 90 | 78 | 6.5 |
| 13 | | 93 | 76 | 6.5 |
| 14 | | 47 | 22 | |
| 15 | 37 | | | |
| 16 | 86 | 70 | | |
| 17* | 44 | | | |
| 18 | | 34 | | |
| 19 | 64 | 35 | | |
| 20* | | 20 | | |
| 22 | | 87 | | 6.58 |
| 23 | | | 15 | |
| 24 | | 81 | | 6.4 |
| 25* | | 11 | | |
| 26 | | 29 | | |
| 28* | | 61 | | 5.8 |
| 29 | 84 | | 43 | |
| 30 | 94 | | 62 | |
| 31 | 94 | | 51 | 5.7 |
| 32 | 92 | 85 | 46 | |
| 33 | 92 | 79 | | |
| 34 | 88 | 56 | | 6.1 |
| 35 | 80 | 47 | | |
| 36 | | 42 | 26 | |
| 37 | 78 | 32 | | |
| 38 | 60 | 30 | | |
| 39 | | | 89 | |
| 40 | 79 | 45 | | 5.8 |
| 41 | | 10 | | |
| 42 | 74 | 46 | | |
| 43 | | 56 | 34 | |
| 44 | | 55 | | |
| 45 | 94 | 73 | | |
| 46 | 23 | | | |
| 47 | 22 | | | |
| 48 | 34 | | | |
| 49 | 18 | | | |
| 50 | | | 66 | |
| 51 | | | 69 | |
| 52 | | | 38 | |
| 54 | | 56 | 40 | |
| 55 | | 59 | 28 | |
| 56 | | 42 | 17 | |
| 57 | | | 87 | 7.0 |
| 58 | | | 47 | 5.95 |
| 59 | | | 95 | 7.5 |
| 60 | | 55 | 28 | |
| 61 | | 70 | 28 | |
| 68 | 100 | | 82 | 6.8 |
| 71 | 100 | | 95 | |
| 72 | | | 100 | |
| 73 | 100 | | 50 | 6.3 |

*Compounds marked with an asterisk were tested using crude SRS-A as the ileum-contracting agent; all other compounds were tested using pure LTD$_4$.

The compounds or formulations of the present invention may be administered by the oral and rectal routes, topically, parenterally, e.g. by injection and by continuous or discontinuous intra-arterial infusion, in the form of, for example, tablets, lozenges, sublingual tablets, sachets, cachets, elixirs, suspensions, aerosols, ointments, for example, containing from 1 to 10% by weight of the active compound in a suitable base, soft and hard gelatin capsules, suppositories, injection solutions and suspensions in physiologically acceptable media, and sterile packaged powders adsorbed onto a support material for making injection solutions. Advantageously for this purpose, compositions may be provided in dosage unit form, preferably each dosage unit containing from 5 to 500 mg. (from 5.0 to 50 mg. in the case of parenteral or inhalation administration, and from 25 to 500 mg. in the case of oral or rectal administration) of a compound of Formula I. Dosages of from 0.5 to 300 mg./kg. per day, preferably 0.5 to 20 mg./kg., of active ingredient may be administered although it will, of course, readily be understood that the amount of the compound or compounds of Formula I actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The formulations of the present invention normally will consist of at least one compound of formula I mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material which serves as a vehicle, excipient or medium for the active therapeutic substance.

Some examples of the diluents or carrier which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention are capsules, tablets, suppositories, injectable solutions, creams and ointments. Especially preferred are formulations for inhalation application, such as an aerosol, and for oral ingestion.

We claim:

1. A compound of the formula I'

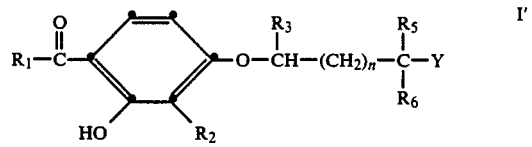

wherein

R$_1$ is hydrogen, C$_1$–C$_6$ alkyl, C$_3$–C$_8$ cycloalkyl, or phenyl;

R$_2$ is hydrogen, C$_1$–C$_6$ alkyl, or C$_2$–C$_6$ alkenyl,

R$_3$ is hydrogen, C$_1$–C$_{10}$ alkyl, phenyl, C$_1$–C$_{10}$ alkyl-substituted phenyl, biphenyl, or benzylphenyl;

R$_5$ and R$_6$ are each independently hydrogen or C$_1$–C$_3$ alkyl;

Y is —CN or —SCN;

and n is 0–10.

2. A compound of claim 1 wherein R$_1$ is methyl and, R$_2$ is propyl.

3. A compound of claim 2 wherein n is 1–4.

4. A compound of claim 3 wherein Y is —CN.

5. A compound of claim 3 wherein Y is —SCN.